(12) United States Patent
Chang et al.

(10) Patent No.: US 12,168,066 B2
(45) Date of Patent: Dec. 17, 2024

(54) HAIR CARE COMPOSITION

(71) Applicant: Conopco, Inc., Englewood Cliffs, NJ (US)

(72) Inventors: Shaokun Chang, Shanghai (CN); Jian Liu, Shanghai (CN); Yingying Pi, Shanghai (CN); Xia Zheng, Shanghai (CN)

(73) Assignee: Conopco, Inc., Englewood Cliffs, NJ (US)

( * ) Notice: Subject to any disclaimer, the term of this patent is extended or adjusted under 35 U.S.C. 154(b) by 677 days.

(21) Appl. No.: 17/416,925

(22) PCT Filed: Jan. 6, 2020

(86) PCT No.: PCT/EP2020/050114
§ 371 (c)(1),
(2) Date: Jun. 21, 2021

(87) PCT Pub. No.: WO2020/144125
PCT Pub. Date: Jul. 16, 2020

(65) Prior Publication Data
US 2022/0040076 A1    Feb. 10, 2022

(30) Foreign Application Priority Data

Jan. 7, 2019  (WO) ................ PCT/CN2019/070654
Feb. 14, 2019 (EP) .................................... 19157051

(51) Int. Cl.
| | | |
|---|---|---|
| A61K 8/49 | (2006.01) | |
| A61K 8/44 | (2006.01) | |
| A61K 8/73 | (2006.01) | |
| A61Q 5/00 | (2006.01) | |
| A61Q 5/02 | (2006.01) | |

(52) U.S. Cl.
CPC ............ *A61K 8/4926* (2013.01); *A61K 8/442* (2013.01); *A61K 8/737* (2013.01); *A61Q 5/006* (2013.01); *A61Q 5/02* (2013.01)

(58) Field of Classification Search
None
See application file for complete search history.

(56) References Cited

U.S. PATENT DOCUMENTS

| | | | |
|---|---|---|---|
| 3,958,581 A | 5/1976 | Abegg et al. | |
| 3,962,418 A | 8/1976 | Birkofer | |
| 4,867,971 A | 9/1989 | Ryan et al. | |
| 6,107,261 A | 8/2000 | Taylor et al. | |
| 6,136,771 A | 10/2000 | Taylor et al. | |
| 6,204,230 B1 | 3/2001 | Taylor et al. | |
| 6,703,427 B2 | 9/2004 | Schmucker et al. | |
| 6,861,397 B2 | 3/2005 | Seitz, Jr. et al. | |
| 8,173,583 B2 | 5/2012 | Garcia Castro et al. | |
| 2003/0133899 A1 | 7/2003 | Fan et al. | |
| 2007/0081953 A1 | 4/2007 | Dahms | |
| 2008/0167284 A1 | 7/2008 | Bhogal et al. | |
| 2011/0064681 A1 | 3/2011 | Wendel et al. | |
| 2013/0150338 A1 | 6/2013 | Ananthapadmanabhan et al. | |
| 2014/0161759 A1 | 6/2014 | Meralli et al. | |
| 2016/0361243 A1 | 12/2016 | Klug et al. | |
| 2018/0110704 A1 | 4/2018 | Zhao et al. | |

FOREIGN PATENT DOCUMENTS

| | | |
|---|---|---|
| CN | 103251523 | 8/2013 |
| CN | 105662929 | 6/2016 |
| CN | 106074252 | 11/2016 |
| CN | 106109259 | 11/2016 |
| CN | 108464953 | 8/2018 |
| CN | 108553335 | 9/2018 |
| CN | 110327282 | 10/2019 |
| EP | 2786742 | 10/2014 |
| JP | 2006525282 | 11/2006 |
| JP | 2010275198 | 12/2010 |
| RU | 2272612 | 3/2006 |
| RU | 2385719 | 4/2010 |
| RU | 2481099 | 5/2013 |
| RU | 2503444 | 1/2014 |
| WO | WO9205764 | 4/1992 |
| WO | WO9631188 | 10/1996 |
| WO | WO9726854 | 7/1997 |
| WO | WO9939683 A1 | 8/1999 |
| WO | WO9955303 | 11/1999 |
| WO | WO03094874 | 11/2003 |
| WO | WO2004098548 | 11/2004 |
| WO | WO2010127924 | 11/2010 |
| WO | WO2011107468 | 9/2011 |
| WO | WO2012022553 | 2/2012 |
| WO | WO12175679 | 12/2012 |
| WO | WO2013011122 | 1/2013 |

(Continued)

OTHER PUBLICATIONS

CN108464953—EPO English Translation (Year: 2018).*

(Continued)

*Primary Examiner* — Kyung S Chang
(74) *Attorney, Agent, or Firm* — Stephanie S. DelPonte

(57) ABSTRACT

A hair care composition is disclosed comprising from 0.5 to 45% by weight of a salt of acyl glutamate and an anti-dandruff agent of piroctone olamine, wherein the salt of acyl glutamate and the anti-dandruff agent are present in a weight ratio of from 5:1 to 50:1, and wherein the composition does not comprise other anionic surfactants in addition to the salt of acyl glutamate.

11 Claims, No Drawings

(56) References Cited

FOREIGN PATENT DOCUMENTS

| WO | WO2015078587 | 6/2015 |
|----|--------------|--------|
| WO | WO2016058837 | 4/2016 |
| WO | WO17102728 | 6/2017 |
| ZA | 97/0696 | 8/1997 |

OTHER PUBLICATIONS

Search Report and Written Opinion in EP19157051; Jun. 3, 2019.
Search Report and Written Opinion in EP19216904; May 12, 2020.
Mintel GNPD; 5D Charm Bright Shampoo; Caile TKCaile; Jan. 14, 2019; pp. 1-2, XP055691647; .; Anonymous retrieved from internet www.gnpd.com Mintel; China.
Mintel GNPD; Chinese Honeylocust Anti-Dandruff Shampoo; Bawang Silicon Free Series; Jun. 1, 2018; pp. 1-4, XP055691656; China.
Mintel GNPD; Scalp Purifying + Bamboo Charcoal Shampoo; Elastine; Mar. 28, 2019; pp. 1-3, XP055691653; China.
Search Report and Written Opinion in PCTEP2020050114; Mar. 27, 2020.
Written Opinion of IPEA (408); Jan. 14, 2021.
Search Report and Written Opinion in PCTEP2020080443; Feb. 8, 2021; World Intellectual Property Org. (WIPO).
Search Report and Written Opinion in PCTEP2020050114.
Mintel GNPD; Perfume Anti-Dandruff Shampoo; Caile N.8+; Mar. 2018; pp. 1-2, Record ID 5549291; China.
Mintel GNPD; Lovefun Gentle & Luxury Care; Amino Acid Shampoo; Jul. 2016; pp. 1-2, Record ID 4110459; China.
Mintel GNPD; Soothing Anti-Dandruff Shampoo; Herborist Basic Series; Mar. 2017; pp. 1-2, Record ID 4690881; China.
Mintel GNPD; Dandruff Killer Shampoo; Dr. Wolff Alpecin; Jan. 2017; pp. 1-2, Record ID 4518065; United Kingdom.
Mintel GNPD; Dandruff Control Shampoo; Grisi Folcress Ozono Shampoo Control Caspa; Jun. 2016; pp. 1-2, Record ID 4085843; Mexico.
Mintel GNPD; Anti-Dandruff Shampoo; Pam & Panorama Arkalia Shampoo con Agente Antiforfora; Sep. 2015; pp. 1-2, Record ID 3449499; Italy.
IPRP2 in PCTEP2020080443; Nov. 5, 2021; World Intellectual Property Org. (WIPO).
IPRP2 in PCTEP2020050114; Mar. 27, 2020; World Intellectual Property Org. (WIPO).

\* cited by examiner

HAIR CARE COMPOSITION

CROSS-REFERENCE TO RELATED APPLICATIONS

This application is a U.S. 371 National Stage Application of PCT International Application No. PCT/EP2020/050114, with international filing date of Jan. 6, 2020, which claims the benefit of and priority to PCT/CN2019/070654 filed Jan. 7, 2019, and European patent application No. 19157051.4 filed Feb. 14, 2019, the contents of which are incorporated herein by reference in their entireties.

TECHNICAL FIELD OF THE INVENTION

This invention is concerned with hair care compositions. More particularly, the present invention is concerned with hair care compositions comprising amino acid surfactants and anti-dandruff agents that provide enhanced deposition of anti-dandruff agents onto hair and/or scalp of an individual.

BACKGROUND OF THE INVENTION

Hair care compositions generally provide cleansing or conditioning benefits or a combination of the two. Such compositions typically comprise one or more cleansing surfactants which generally aid in cleaning the hair and the scalp free of undesirable soil, particles and fatty matter.

Anti-dandruff benefit has also been provided through hair care compositions. Dandruff is an issue that affects many people globally. The condition is manifested by the shedding of clumps of dead skin cells from the scalp. These are white in colour and provide an aesthetically displeasing appearance. A factor that contributes to dandruff is certain members of the Malassezia yeasts. To combat these, anti-dandruff products have included certain anti-dandruff agents which have anti-fungal activity, for example, piroctone olamine (octopirox), azole based anti-fungal agents (e.g. climbazole, ketoconazole), selenium sulfide or combinations thereof. Such a product has to perform as a hair cleansing shampoo, while mitigating the causes of dandruff. Many anti-dandruff shampoos, however, do not provide sufficient anti-dandruff agent deposition during the shampooing process. The anti-dandruff agents are simply rinsed away during shampooing and therefore provide little or no anti-dandruff efficacy. Therefore, it is always desired to improve the deposition of anti-dandruff agents to maximize the effectiveness of such anti-dandruff agents.

Surfactants such as cationic, anionic, amphoteric, non-ionic surfactants are widely used in hair care compositions. Anionic surfactants such as sulphated surfactants generally exhibit superior cleansing and foaming properties and are thus typically incorporated into such compositions. However, sulphated surfactants like sodium lauryl ether sulphate (SLES) tend to be harsh on the skin and may adversely affect the deposition of anti-dandruff agents. Therefore, there is a need to find milder surfactants which are not as harsh and irritating on skin while aiding deposition of anti-dandruff agents.

Tests and Definitions

Hair Care Composition

"Hair care composition", as used herein, is meant to include a composition for topical application to hair and/or scalp of mammals, especially humans. Such a composition may be generally classified as leave-on or rinse off, and includes any product applied to a human body for also improving appearance, cleansing, odor control or general aesthetics. The composition of the present invention can be in the form of a liquid, lotion, cream, foam, scrub, gel, or bar. Non-limiting examples of such compositions include leave-on hair lotions, creams, and rinse-off shampoos, conditioners, shower gels, or toilet bar. The composition of the present invention is preferably a rinse-off composition, especially preferred being a shampoo or a conditioner and most preferably a shampoo.

Cationic Charge Density

"Cationic charge density", as used herein, refers to the number of cationic charges per weight unit of a given polymer. Cationic charge density can be calculated from the degree of substitution as described in WO 2013/011122, the disclosure of which is hereby incorporated by reference in its entirety but especially page 8 lines 8-17. For example, for cationically-modified guar polymer obtained by reacting with 2,3-epoxypropyltrimethylammonium chloride, the cationic charge density may be calculated from the DS using the following equation:

$$\text{Cationic charge density in milliequivalents per gram(meq/g)} = \frac{DS \times 1000}{162 + 151 \times DS}$$

Water-Insoluble

"Water-insoluble", as used herein, refers to the solubility of a material in water at 25° C. and atmospheric pressure being 0.1% by weight or less.

Molecular Weight

"Molecular weight", as used herein, refers to the weight average molecular mass of a given polymer. The weight average molecular weight (WAVG MW) of a given polymer is determined by SEC (Size Exclusion Chromatography) analysis using absolute calibration (universal calibration). Polysaccharide standards pulluan and dextran were used for calibration.

Miscellaneous

Except in the examples, or where otherwise explicitly indicated, all numbers in this description indicating amounts of material or conditions of reaction, physical properties of materials and/or use may optionally be understood as modified by the word "about".

All amounts are by weight of the final hair care composition, unless otherwise specified. It should be noted that in specifying any ranges of values, any particular upper value can be associated with any particular lower value.

For the avoidance of doubt, the word "comprising" is intended to mean "including" but not necessarily "consisting of" or "composed of". In other words, the listed steps or options need not be exhaustive.

The disclosure of the invention as found herein is to be considered to cover all embodiments as found in the claims as being multiply dependent upon each other irrespective of the fact that claims may be found without multiple dependency or redundancy.

Where a feature is disclosed with respect to a particular aspect of the invention (for example a composition of the invention), such disclosure is also to be considered to apply to any other aspect of the invention (for example a method of the invention) mutatis mutandis.

SUMMARY OF THE INVENTION

In a first aspect, the present invention is directed to a hair care composition comprising:
(a) from 0.5 to 45% by weight of a salt of acyl glutamate;
(b) an anti-dandruff agent of piroctone olamine;
wherein the salt of acyl glutamate and the anti-dandruff agent are present in a weight ratio of from 5:1 to 50:1; and wherein the composition does not comprise other anionic surfactants in addition to the salt of acyl glutamate.

In a second aspect, the present invention is directed to a packaged hair care product comprising the hair care composition of the first aspect of this invention.

In a third aspect, the present invention is directed to a method of depositing anti-dandruff agents onto scalp comprising the step of applying the hair care composition of any embodiment of the first aspect of this invention onto scalp surfaces of an individual.

All other aspects of the present invention will more readily become apparent upon considering the detailed description and examples which follow.

DETAILED DESCRIPTION

The salt of acyl glutamate is an amino acid surfactant derived from glutamate. It is used as a mild anionic surfactant to alleviate harshness and irritations. The chemical structure of the salt of acyl glutamate suitable for use in compositions of the present invention is represented by the general formula (I), (II) or (III):

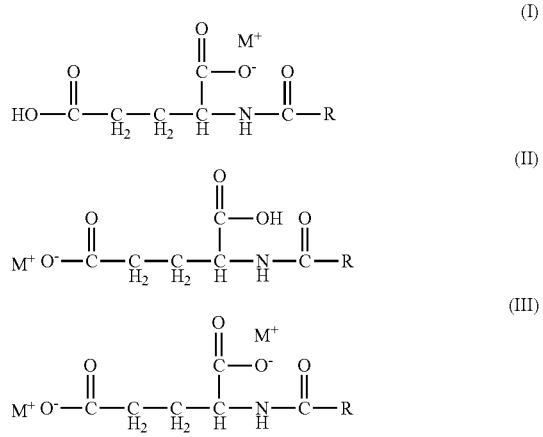

wherein R is alkyl or alkenyl group having 7 to 20 carbons, preferably 8 to 17 carbons, and M is a solubilising cation comprising sodium, potassium, ammonium, substituted ammonium or mixtures thereof, preferably sodium.

Suitable examples of the salt of acyl glutamate that may be used in this invention include, but not limited to, sodium capryloyl glutamate, sodium cocoyl glutamate, sodium lauroyl glutamate, sodium myristoyl glutamate, sodium olivoyl glutamate, sodium palmitoyl glutamate, sodium stearoyl glutamate, sodium undecylenoyl glutamate, potassium capryloyl glutamate, potassium cocoyl glutamate, potassium lauroyl glutamate, potassium myristoyl glutamate, potassium stearoyl glutamate, potassium undecylenoyl glutamate, dipotassium capryloyl glutamate, dipotassium undecylenoyl glutamate, disodium capryloyl glutamate, disodium cocoyl glutamate, disodium lauroyl glutamate, disodium stearoyl glutamate, disodium undecylenoyl glutamate or mixtures thereof. Particularly preferred are sodium cocoyl glutamate, sodium lauroyl glutamate or mixtures thereof.

The hair care composition of the present invention comprises the salt of acyl glutamate in an amount of from 0.5 to 45%, preferably from 1 to 30% and more preferably from 5 to 20%, based on total weight of the hair care composition and including all ranges subsumed therein.

The hair care composition of the present invention does not comprise other anionic surfactants in addition to the salt of acyl glutamate which is included in the composition. If other anionic surfactants are present, it is preferred that the salt of acyl glutamate is at least 75% by weight of the anionic surfactants in the composition, more preferably from 80 to 100%, and most preferably from 95 to 100%, based on total weight of the anionic surfactants in the composition.

If the hair care composition comprises other anionic surfactants in addition to the salt of acyl glutamate, it is preferred if they are present in an amount less than 0.01% by weight of the composition, more preferably less than 0.001%. Non-limiting examples of other anionic surfactants are alkyl sulphates, alkyl ether sulphates, alkaryl sulphonates, alkanoyl isethionates, alkyl succinates, alkyl sulphosuccinates, alkyl ether sulphosuccinates, N-alkyl sarcosinates, alkyl phosphates, alkyl ether phosphates, and alkyl ether carboxylic acids and salts thereof, especially their sodium, magnesium, ammonium and mono-, di- and triethanolamine salts. The alkyl and acyl groups generally contain from 8 to 18, preferably from 10 to 16 carbon atoms and may be unsaturated. The alkyl ether sulphates, alkyl ether sulphosuccinates, alkyl ether phosphates and alkyl ether carboxylic acids and salts thereof may contain from 1 to 20 ethylene oxide or propylene oxide units per molecule. Typical examples of other anionic surfactants include, but not limited to, sodium oleyl succinate, ammonium lauryl sulphosuccinate, sodium lauryl sulphate, sodium lauryl ether sulphate, sodium lauryl ether sulphosuccinate, ammonium lauryl sulphate, sodium dodecylbenzene sulphonate, triethanolamine dodecylbenzene sulphonate, sodium cocoyl isethionate, sodium lauryl isethionate, lauryl ether carboxylic acid, sodium N-lauryl sarcosinate or mixtures thereof.

In a preferred embodiment, the hair care composition may further comprise co-surfactants such as amphoteric and zwitterionic surfactants in addition to the salts of acyl glutamate that is included in the composition to provide mildness to the composition. Suitable examples include alkyl amine oxides, alkyl betaines, alkyl amidopropyl betaines, alkyl sulphobetaines (sultaines), alkyl amphoacetates, alkyl amphopropionates, alkyl amidopropyl hydroxysultaines, wherein the alkyl group has from 8 to 19 carbon atoms. Preferably, the co-surfactant is a betaine surfactant. Cocamidopropyl betaine (CAPB) is particularly preferred.

When used, the co-surfactant typically makes up from 0.1 to 15%, more preferably from 0.5 to 8% and most preferably from 1 to 4% by weight of the hair care composition, based on total weight of the hair care composition and including all ranges subsumed therein.

The hair care composition comprises anti-dandruff agents, which are compounds that are active against dandruff and are typically anti-microbial agents and preferably anti-fungal agents. The anti-dandruff agent is piroctone olamine.

Typically, the hair care composition of the invention comprises the anti-dandruff agent in an amount of from 0.01 to 10%, more preferably from 0.01 to 5%, more preferably still from 0.05 to 2%, and most preferably from 0.05 to 1.5%, based on total weight of the hair care composition and including all ranges subsumed therein.

The hair care composition comprises the salt of acyl glutamate and the anti-dandruff agent in a weight ratio of from 5:1 to 50:1, preferably from 5:1 to 30:1, more preferably from 10:1 to 25:1, and most preferably from 15:1 to 25:1.

The composition may further comprise a cationic polymer. Suitable cationic polymers may be homopolymers or be formed from two or more types of monomers. The molecular weight of the polymer will generally be between 5,000 and 10,000,000 g/mol, typically at least 10,000 g/mol and preferably from 100,000 to 2,000,000 g/mol.

The polymers will have cationic nitrogen containing groups such as quaternary ammonium or protonated amino groups, or a mixture thereof. The cationic nitrogen containing group will generally be present as a substituent on a fraction of the total monomer units of the cationic polymer. Thus when the polymer is not a homopolymer it can contain spacer non-cationic monomer units. The ratio of the cationic to non-cationic monomer units is selected to give a polymer having a cationic charge density in the required range.

Suitable cationic polymers include, for example, copolymers of vinyl monomers having cationic amine or quaternary ammonium functionalities with water soluble spacer monomers such as (meth)acrylamide, alkyl and dialkyl (meth) acrylamides, alkyl (meth)acrylate, vinyl caprolactone and vinyl pyrrolidine. The alkyl and dialkyl substituted monomers preferably have C1-C7 alkyl groups, more preferably C1-C3 alkyl groups. Other suitable spacers include vinyl esters, vinyl alcohol, maleic anhydride, propylene glycol and ethylene glycol.

Preferably, the cationic polymer is a cationic polysaccharide polymer such as cationic cellulose derivatives, cationic starch derivatives, and cationic guar gum derivatives. Suitably, such cationic polysaccharide polymers have a molecular weight of from 100,000 g/mol to 2,300,000 g/mol, more preferably from 150,000 g/mol to 2,000,000 g/mol. Such cationic polysaccharide polymers preferably have a cationic charge density from 0.1 to 4 meq/g.

Cationic polysaccharide polymers suitable for use in compositions of this invention include those represented by the general formula:

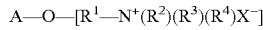

A—O—[R$^1$—N$^+$(R$^2$)(R$^3$)(R$^4$)X$^-$]

wherein: A is an anhydroglucose residual group, such as a starch or cellulose anhydroglucose residual. R$^1$ is an alkylene, oxyalkylene, polyoxyalkylene, or hydroxyalkylene group, or combination thereof. R$^2$, R$^3$ and R$^4$ independently represent alkyl, aryl, alkylaryl, arylalkyl, alkoxyalkyl, or alkoxyaryl groups, each group containing up to about 18 carbon atoms. The total number of carbon atoms for each cationic moiety (i.e., the sum of carbon atoms in R$^2$, R$^3$ and R$^4$) is preferably about 20 or less, and X is an anionic counterion.

Cationic cellulose is available from Amerchol Corp. (Edison, NJ, USA) in their Polymer JR (trade mark) and LR (trade mark) series of polymers, as salts of hydroxyethyl cellulose reacted with trimethyl ammonium substituted epoxide, referred to in the industry (CTFA) as Polyquaternium 10. Another type of cationic cellulose includes the polymeric quaternary ammonium salts of hydroxyethyl cellulose reacted with lauryl dimethyl ammonium-substituted epoxide, referred to in the industry (CTFA) as Polyquaternium 24. These materials are available from Amerchol Corp. (Edison, NJ, USA) under the tradename Polymer LM-200.

Other suitable cationic polysaccharide polymers include quaternary nitrogen-containing cellulose ethers (e.g. as described in U.S. Pat. No. 3,962,418) and copolymers of etherified cellulose and starch (e.g. as described in U.S. Pat. No. 3,958,581).

A particularly preferred type of cationic polysaccharide polymer that can be used in compositions of the present invention is a cationic guar gum derivative, such as guar hydroxypropyltrimonium chloride (for example, commercially available from Solvay in their Jaguar trademark series or from Ashland in their N-Hance trademark series). Examples of such materials are Jaguar® C-13S, Jaguar® C-14S, Jaguar® C-17, Jaguar® Excel, Jaguar® C-162, Jaguar® C-500, Jaguar® Optima, Jaguar® LS, N-Hance™ BF17, N-Hance™ BF13 and N-Hance™ CCG45.

Mixtures of any of the above cationic polymers may be used. The cationic polymer preferably comprises cationic cellulose derivatives, cationic guar gum derivatives or mixtures thereof. Guar hydroxypropyltrimonium chloride is particularly preferred.

When used, the cationic polymer will generally be present in the hair care composition of the present invention in an amount of from 0.001 to 1% by weight of the hair care composition, more preferably from 0.01 to 0.5%, and most preferably from 0.03 to 0.3%, based on total weight of the hair care composition and including all ranges subsumed therein.

The pH of the composition is preferably equal to or higher than 4.0, more preferably in the range of 4.0 to 7.0.

The hair care composition may additionally comprise a conditioning agent to provide conditioning benefit. Typically, the most popular conditioning agents used in hair care compositions are water-insoluble oily materials such as mineral oils, naturally occurring oils such as triglycerides and silicone polymers. Conditioning benefit is achieved by the oily material being deposited onto the hair resulting in the formation of a film, which makes the hair easier to comb when wet and more manageable when dry. Preferably, the conditioning agent is non-volatile, meaning that it has a vapour pressure of less than 1000 Pa at 25° C.

Preferably, the hair care composition comprises discrete dispersed droplets of a water-insoluble conditioning agent, which has a mean droplet diameter ($D_{3,2}$) of less than 15 microns, preferably less than 10 microns, more preferably less than 5 microns, most preferably less than 3 microns. The mean droplet diameter ($D_{3,2}$) of a water-insoluble conditioning agent may be measured by means of a laser light scattering technique, for example using a 2600D Particle Sizer from Malvern Instruments.

The water-insoluble conditioning agent may include non-silicone conditioning agent comprising non-silicone oily or fatty materials such as hydrocarbon oils, fatty esters and mixtures thereof. Preferably, the water-insoluble conditioning agent is emulsified silicone oil.

Suitable silicones include polydiorganosiloxanes, in particular polydimethylsiloxanes which have the CTFA designation dimethicone. Also suitable for use in compositions of this invention (particularly shampoos and conditioners) are polydimethyl siloxanes having hydroxyl end groups, which have the CTFA designation dimethiconol. Also suitable for use in compositions of this invention are silicone gums having a slight degree of cross-linking, as are described for example in WO 96/31188. Preferably, the silicone oil comprises dimethicone, dimethiconol or a mixture thereof.

The viscosity of the emulsified silicone itself (not the emulsion or the final hair care composition) is typically at least 10,000 cSt (centi-Stokes=mm$^2 \cdot$S$^{-1}$) at 25° C., preferably at least 60,000 cSt, most preferably at least 500,000 cSt, ideally at least 1,000,000 cSt. Preferably the viscosity does not exceed $10^9$ cSt for ease of formulation. Suitable methods for measuring the kinematic viscosity of silicone oils are known to those skilled in the art, e.g. capillary viscometers. For high viscosity silicones, a constant stress rheometer can be used to measure viscosity.

Suitable emulsified silicones for use in the hair care compositions of this invention are available as pre-formed silicone emulsions from suppliers of silicones such as Dow Corning and GE silicones. The use of such pre-formed silicone emulsion is preferred for ease of processing and control of silicone particle size. Such pre-formed silicone emulsions will typically additionally comprise a suitable emulsifier, and may be prepared by a chemical emulsification process such as emulsion polymerisation, or by mechanical emulsification using a high shear mixer.

Examples of suitable pre-formed silicone emulsions include DC1785, DC1788, DC7128, all available from Dow Corning. These are emulsions of dimethiconol/dimethicone.

Another class of silicones which may be used are functionalized silicones such as amino functional silicones, meaning a silicone containing at least one primary, secondary or tertiary amine group, or a quaternary ammonium group. Examples of suitable amino functional silicones include polysiloxanes having the CTFA designation "amodimethicone."

Preferably, silicone emulsion droplets are blended with certain types of surface active block polymers of a high molecular weight to form silicone emulsions, as described for example in WO03/094874. One preferred form of the surface active block polymer having polyoxypropylene and polyoxyethylene groups as the hydrophobic and hydrophilic part respectively has formula I and has the CTFA designation poloxamer, known commercially under the trade name "Pluronic" from BASF.

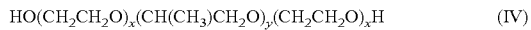

$$HO(CH_2CH_2O)_x(CH(CH_3)CH_2O)_y(CH_2CH_2O)_xH \qquad (IV)$$

Suitably, the mean value of x in formula (IV) is 4 or more, preferably 8 or more, more preferably 25 or more, yet more preferably 50 or more and most preferably 80 or more. The mean value of x is typically no greater than 200. Suitably, the mean value of y is 25 or more, preferably 35 or more, more preferably 45 or more and most preferably 60 or more. The mean value of y is typically no greater than 100.

Another preferred form of the surface active block polymer is according to formula (V) and has the CTFA designation Poloxamine. Those are commercially available under the trade name "Tetronic" from BASF.

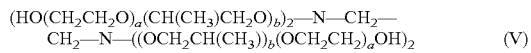

$$(HO(CH_2CH_2O)_a(CH(CH_3)CH_2O)_b)_2-N-CH_2-$$
$$CH_2-N-((OCH_2CH(CH_3))_b(OCH_2CH_2)_aOH)_2 \qquad (V)$$

Suitably, the mean value of a is 2 or more, preferably 4 or more, more preferably 8 or more, even more preferably 25 or more and most preferably 40 or more. The mean value of a is typically no greater than 200. The mean value of b is suitably 6 or more, preferably 9 or more, more preferably 11 or more and most preferably 15 or more. The mean value of b is typically no greater than 50.

Preferably, the surface active block polymer is poloxamer and/or poloxamine, more preferably, the surface active block polymer is poloxamer.

Preferably, the surface active block polymer is blended with dimethicone. The weight ratio of dimethicone to surface active block polymer in the blend is preferably in the range from 2:1 to 200:1, more preferably from 5:1 to 50:1, even more preferably from 10:1 to 40:1, most preferably from 15:1 to 30:1.

The water-insoluble conditioning agent is generally present in hair care composition of this invention in an amount from 0.05 to 15%, preferably from 0.1 to 10%, more preferably from 0.5 to 8%, most preferably from 1 to 5%, based on total weight of the hair care composition and including all ranges subsumed therein.

Preferably the composition of the invention further comprises a suspending agent. Suitable suspending agents are selected from polyacrylic acids, cross-linked polymers of acrylic acid, copolymers of acrylic acid with a hydrophobic monomer, copolymers of carboxylic acid-containing monomers and acrylic esters, cross-linked copolymers of acrylic acid and acrylate esters, heteropolysaccharide gums and crystalline long chain acyl derivatives. The long chain acyl derivative is desirably selected from ethylene glycol stearate, alkanolamides of fatty acids having from 16 to 22 carbon atoms and mixtures thereof. Ethylene glycol distearate and polyethylene glycol 3 distearate are preferred long chain acyl derivatives, since these impart pearlescence to the composition. Polyacrylic acid is available commercially as Carbopol 420, Carbopol 488 or Carbopol 493. Polymers of acrylic acid cross-linked with a polyfunctional agent may also be used; they are available commercially as Carbopol 910, Carbopol 934, Carbopol 941 and Carbopol 980. An example of a suitable copolymer of a carboxylic acid containing monomer and acrylic acid esters is Carbopol 1342. All Carbopol (trademark) materials are available from Goodrich.

Suitable cross-linked polymers of acrylic acid and acrylate esters are Pemulen TR1 or Pemulen TR2. A suitable heteropolysaccharide gum is xanthan gum, for example that available as Kelzan mu.

Mixtures of any of the above suspending agents may be used. Preferred is a mixture of cross-linked polymer of acrylic acid and crystalline long chain acyl derivative.

The suspending agent is generally present in hair care composition of this invention in an amount of from 0.1 to 10%, more preferably from 0.5 to 6%, and most preferably from 0.5 to 4%, based on total weight of the hair care composition and including all ranges subsumed therein.

Preservatives may also be incorporated into the hair care composition of this invention to protect against the growth of potentially harmful microorganisms. Suitable traditional preservatives include alkyl esters of parahydroxybenzoic acid, hydantoin derivatives, propionate salts, and a variety of quaternary ammonium compounds. Illustrative yet non-limiting examples of the types of preservatives that may be used in this invention include, for examples, phenoxyethanol, sodium salicylate, methyl paraben, butyl paraben, propyl paraben, diazolidinyl urea, sodium dehydroacetate, benzyl alcohol, sodium benzoate, iodopropynyl butylcarbamate, caprylyl glycol, disodium EDTA or mixtures thereof. In an especially preferred embodiment, the preservative is phenoxyethanol, sodium salicylate or a mixture thereof. Preservatives are preferably employed in amounts ranging from 0.01 to 2% by weight of the hair care composition.

The hair care composition of the present invention may contain other ingredients which are common in the art to enhance physical properties and performances. Suitable ingredients include but are not limited to fragrance, dyes and pigments, pH adjusting agents, pearlescers or opacifiers, viscosity modifiers, thickeners, and natural hair nutrients such as botanicals, fruit extracts, sugar derivatives and amino acids.

The compositions of the invention are primarily intended for topical application to scalp and/or at least a portion of the hair of an individual, either in rinse-off or leave-on compositions, preferably in rinse-off compositions like shampoos.

The following examples are provided to facilitate an understanding of the present invention. The examples are not provided to limit the scope of the claims.

EXAMPLES

Example 1

This example demonstrated the effect of anionic surfactants on the deposition of anti-dandruff agents onto scalp. Compositions were prepared according to the formulations detailed in Table 1. All ingredients are expressed by weight percent of the total formulation, and as level of active ingredient.

TABLE 1

| Ingredient | Samples | | | |
|---|---|---|---|---|
| | 1 | 2 | 3 | 4 |
| Water | Balance | Balance | Balance | Balance |
| Sodium salicylate | 0.30 | 0.30 | 0.30 | 0.30 |
| Disodium EDTA | 0.05 | 0.05 | 0.05 | 0.05 |
| Guar hydroxypropyltrimonium chloride[a] | 0.20 | 0.20 | 0.20 | 0.20 |
| Phenoxyethanol | 0.50 | 0.50 | 0.50 | 0.50 |
| Piroctone olamine (Octopirox) | 0.50 | 0.50 | 0.50 | 0.50 |
| Sodium laureth sulphate (2EO) | 10.00 | — | — | — |
| Sodium cocoyl glutamate | — | 10.00 | — | — |
| Sodium lauroyl glutamate | — | — | 10.00 | — |
| Sodium cocoyl glycinate | — | — | — | 10.00 |
| Perfume | 0.75 | 0.75 | 0.75 | 0.75 |
| Sodium chloride | 1.00 | 1.00 | 1.00 | 1.00 |

[a]The cationic guar has a weight average molecular weight of from 1.0 to 1.5 million g/mol and a degree of substitution of from 0.16 to 0.20 sourced from Lamberti Methods About 0.2 grams of the test sample was taken on artificial skin (VITRO-SKIN from IMS testing group). This was diluted with 1.8 mL water and rubbed with a plastic rod for 30 seconds. The artificial skin surface was then rinsed twice with water, first time with 4 mL water for 30 second and then again with 4 mL water for 30 seconds. The deposition of octopirox (OCT) on the skin (10.75 cm$^2$ per plate) was measured using HPLC method.

Results

The average deposition (of five such experiments) are summarized in Table 2 (error represents standard deviation for duplicate measurements).

TABLE 2

| Samples | 1 | 2 | 3 | 4 |
|---|---|---|---|---|
| OCT Deposition (μg/plate) | 10.13 ± 1.80 | 22.06 ± 4.74 | 26.03 ± 5.12 | 13.37 ± 1.16 |

The results reported in table 2 showed that samples 2 and 3 (consistent with the invention) provided significantly better ($p<0.05$) octopirox deposition compared to samples 1 and 4.

Example 2

This example demonstrated the weight ratio of acyl glutamate salts to anti-dandruff agents can affect the deposition of anti-dandruff agents onto scalp. Compositions were prepared according to the formulations detailed in Tables 3 and 4. All ingredients are expressed by weight percent of the total formulation, and as level of active ingredient.

TABLE 3

| Ingredient | Samples | | | | |
|---|---|---|---|---|---|
| | 5 | 6 | 7 | 8 | 9 |
| Water | Balance | Balance | Balance | Balance | Balance |
| Sodium salicylate | 0.30 | 0.30 | 0.30 | 0.30 | 0.30 |
| Disodium EDTA | 0.05 | 0.05 | 0.05 | 0.05 | 0.05 |
| Guar hydroxypropyltrimonium chloride[a] | 0.20 | 0.20 | 0.20 | 0.20 | 0.20 |
| Phenoxyethanol | 0.50 | 0.50 | 0.50 | 0.50 | 0.50 |
| Piroctone olamine (Octopirox) | 0.50 | 0.50 | 0.50 | 0.50 | 0.50 |
| Sodium laureth sulphate (2EO) | 10.00 | — | 9.25 | — | 9.25 |
| Sodium cocoyl glutamate | — | 10.00 | 0.75 | — | — |
| Sodium lauroyl glutamate | — | — | — | 10.00 | 0.75 |
| Perfume | 0.75 | 0.75 | 0.75 | 0.75 | 0.75 |
| Sodium chloride | 1.00 | 1.00 | 1.00 | 1.00 | 1.00 |

TABLE 4

| Ingredient | Samples | |
|---|---|---|
| | 10 | 11 |
| Water | Balance | Balance |
| Sodium salicylate | 0.30 | 0.30 |
| Disodium EDTA | 0.05 | 0.05 |
| Guar hydroxypropyltrimonium chloride[a] | 0.20 | 0.20 |
| Phenoxyethanol | 0.50 | 0.50 |
| Piroctone olamine (Octopirox) | 0.50 | 0.50 |
| Sodium laureth sulphate (2EO) | — | 0.715 |
| Sodium cocoyl glutamate | 2.50 | 1.785 |
| Perfume | 0.75 | 0.75 |
| Sodium chloride | 1.00 | 1.00 |

Methods

The same protocol was used to evaluate the deposition of anti-dandruff agents onto scalp as described in Example 1.

Results

The average deposition (of five such experiments) are summarized in Tables 5 and 6 (error represents standard deviation for duplicate measurements).

TABLE 5

| Samples | 5 | 6 | 7 | 8 | 9 |
|---|---|---|---|---|---|
| OCT Deposition (µg/plate) | 16.68 ± 2.65 | 31.21 ± 2.34 | 12.09 ± 1.21 | 37.54 ± 4.91 | 16.85 ± 2.41 |

TABLE 6

| Samples | 10 | 11 |
|---|---|---|
| OCT Deposition (µg/plate) | 36.52 ± 4.46 | 28.20 ± 1.15 |

Samples 6 and 8 provided significantly better ($p<0.01$) octopirox deposition compared to other samples. The results showed that the weight ratio of acyl glutamate salts to octopirox was important for the deposition of octopirox. For example, sample 6 comprising a higher weight ratio of acyl glutamate salts to octopirox provided significantly better ($p<0.01$) octopirox deposition than sample 7. The same result was also observed for samples 8 and 9.

Sample 10 comprising acyl glutamate salts and octopirox at a weight ratio of 5:1 showed a significantly better ($p<0.05$) octopirox deposition than sample 11.

Example 3

This example demonstrated the presence of additional anionic surfactants can affect the deposition of anti-dandruff agents onto scalp. Compositions were prepared according to the formulations detailed in Table 7. All ingredients are expressed by weight percent of the total formulation, and as level of active ingredient.

TABLE 7

| | Samples | | | |
|---|---|---|---|---|
| Ingredient | 12 | 13 | 14 | 15 |
| Water | Balance | Balance | Balance | Balance |
| Sodium salicylate | 0.30 | 0.30 | 0.30 | 0.30 |
| Disodium EDTA | 0.05 | 0.05 | 0.05 | 0.05 |
| Guar hydroxypropyltrimonium chloride[a] | 0.20 | 0.20 | 0.20 | 0.20 |
| Phenoxyethanol | 0.50 | 0.50 | 0.50 | 0.50 |
| Piroctone olamine (Octopirox) | 0.50 | 0.50 | 0.50 | 0.50 |
| Sodium cocoyl glutamate | 10.00 | 6.25 | — | — |
| Sodium lauroyl glutamate | — | — | 10.00 | 6.25 |
| Lauryl sulfate monoethanolamine salt | — | 3.75 | — | 3.75 |
| Perfume | 0.75 | 0.75 | 0.75 | 0.75 |
| Sodium chloride | 1.00 | 1.00 | 1.00 | 1.00 |

Methods

The same protocol was used to evaluate the deposition of anti-dandruff agents onto scalp as described in Example 1.

Results

The average deposition (of five such experiments) are summarized in Table 8 (error represents standard deviation for duplicate measurements).

TABLE 8

| Samples | 12 | 13 | 14 | 15 |
|---|---|---|---|---|
| OCT Deposition (µg/plate) | 17.63 ± 1.28 | 6.97 ± 0.70 | 19.58 ± 2.15 | 10.99 ± 1.75 |

It can be seen from the results that sample 13 comprising other anionic surfactants in addition to the salt of acyl glutamate provided inferior deposition of octopirox to sample 12. The same result was also observed for samples 14 and 15.

The invention claimed is:

1. A hair care composition comprising:
   (a) from 0.5 to 45% by weight of an anionic surfactant wherein the anionic surfactant is a salt of acyl glutamate selected from sodium cocoyl glutamate, sodium lauroyl glutamate, and combinations thereof;
   (b) from 0.05 to 1.5% by weight of piroctone olamine; and
   (c) from 0.03 to 0.3% by weight of a cationic polymer wherein the cationic polymer is guar hydroxypropyltrimonium chloride,
   wherein the salt of acyl glutamate and the piroctone olamine are present in a weight ratio of from 5:1 to 50:1; and
   wherein the composition does not comprise other anionic surfactants in addition to the salt of acyl glutamate.

2. The hair care composition according to claim 1, wherein the composition comprises the salt of acyl glutamate in an amount of from 1 to 30%.

3. The hair care composition according to claim 1, wherein the salt of acyl glutamate and the piroctone olamine are present in a weight ratio of from 5:1 to 30:1.

4. The hair care composition according to claim 1 further comprising a co-surfactant selected from an amphoteric surfactant, a zwitterionic surfactant, and combinations thereof.

5. The hair care composition according to claim 4, wherein the zwitterionic surfactant is a betaine surfactant.

6. The hair care composition according to claim 1, wherein the composition is a shampoo.

7. A method of depositing an anti-dandruff agent onto scalp comprising:
   applying the hair care composition according to claim 1 onto scalp surfaces of an individual, and
   rinsing the surfaces with water
   wherein the anti-dandruff agent is piroctone olamine.

8. The hair care composition according to claim 2, wherein the composition comprises the salt of acyl glutamate in an amount of from 5 to 20%.

9. The hair care composition according to claim 3, wherein the salt of acyl glutamate and the piroctone olamine are present in a weight ratio of from 10:1 to 25:1.

10. The hair care composition according to claim 5, wherein the zwitterionic surfactant is cocamidopropyl betaine.

11. A hair care composition comprising:
   (a) from 5 to 20% by weight of an anionic surfactant wherein the wherein the anionic surfactant is a salt of acyl glutamate, wherein the salt of acyl glutamate is sodium cocoyl glutamate;
   (b) from 0.05 to 1.5% by weight of piroctone olamine; and
   (c) from 0.03 to 0.3% by weight of a cationic polymer wherein the cationic polymer is guar hydroxypropyltrimonium chloride, wherein the sodium cocoyl glutamate and the piroctone olamine are present in a weight ratio of from 15:1 to 25:1; and wherein the composition does not comprise other anionic surfactants in addition to the sodium cocoyl glutamate.

* * * * *